United States Patent [19]
Doran, III et al.

[11] Patent Number: 5,204,005
[45] Date of Patent: Apr. 20, 1993

[54] REVERSED PHASE CHROMATOGRAPHIC PROCESS

[75] Inventors: Narciso O. Doran, III, Bridgeton; Thomas J. Dunn, Cedar Hill; Mills T. Kneller, University City; Youlin Lin, Chesterfield; David H. White, Florissant; David Ming-Lee Wong, Chesterfield, all of Mo.

[73] Assignee: Mallinckrodt, Inc., St. Louis, Mo.

[21] Appl. No.: 646,836

[22] Filed: Jan. 28, 1991

Related U.S. Application Data

[63] Continuation-in-part of Ser. No. 484,261, Feb. 26, 1990, abandoned.

[51] Int. Cl.$^5$ ............................................. B01D 15/08
[52] U.S. Cl. ................................... 210/656; 210/635; 424/5
[58] Field of Search ............... 210/635, 656, 198.2; 564/156; 424/5

[56] References Cited

U.S. PATENT DOCUMENTS 4,396,598  8/1983  Lin .......................................... 424/5

FOREIGN PATENT DOCUMENTS 3110737  10/1982  Fed. Rep. of Germany .

OTHER PUBLICATIONS

Nettleton, Jr., "Preparative Liquid Chromatography. I. Approaches Utilizing Highly Compressed Beds. ", *Journal of Liquid Chromatography*, 4(Suppl. 1), pp. 141–173 (1981).

Jones, K., "Process Scale High Performance Liquid Chromatography Part II; Dissolution of Silica Matrices", *Chromatographia* vol. 25, No. 5, pp. 443–446, (May 1988).

*Primary Examiner*—Wilbur Bascomb, Jr.
*Assistant Examiner*—Neil M. McCarthy
*Attorney, Agent, or Firm*—Senninger, Powers, Leavitt & Roedel

[57] ABSTRACT

An improved process for the reversed phase chromatographic decolorization, separation, and purification of water-soluble, nonionic contrast media compounds from solutions containing nonionic compound impurities involves the steps of (a) packing a chromatographic column with a chromatographic packing material; (b) passing through the column a solution containing a water-soluble, nonionic contrast media compound and nonionic compounds as impurities at a loading ratio between approximately 10 to 1 and 1.5 to 1 wt. packing material/total wt. nonionic compounds; and (c) eluting the column to produce an eluate containing substantially pure, water-soluble, nonionic contrast media compound or MRI agent. The process can be economically practiced on a factory scale and efficiently removes non-polar impurities difficult to remove by conventional methods.

34 Claims, No Drawings

REVERSED PHASE CHROMATOGRAPHIC PROCESS

REFERENCE TO CROSS-RELATED APPLICATION

This application is a continuation-in-part of application Ser. No. 484,261 filed Feb. 26, 1990, abandoned.

BACKGROUND OF THE INVENTION

This invention relates to the decolorization, separation, and purification of water-soluble, nonionic compounds from solutions containing nonionic compound impurities and, more particularly, the decolorization, separation, and purification of water-soluble, nonionic contrast media compounds from nonionic compound impurities by large, factory scale reversed phase chromatography.

In the preparation of nonionic compounds, such as nonionic X-ray contrast media and magnetic resonance imaging (MRI) agents, nonionic impurities are produced which are difficult to remove in an efficient and economical manner. Nonionic, low osmolar X-ray contrast media and MRI agents have become generally regarded as being safe and providing advantageous contrast enhancement in various radiographic procedures. However, such nonionic X-ray contrast media are more costly than ionic X-ray contrast media because of the complexity of the processes required for their synthesis and also because in many instances, the nonionic, non-polar impurities associated therewith require multiple crystallization and/or precipitation procedures for satisfactory removal. Thus, in the preparation of the nonionic contrast agents iohexol (N,N'-bis(2,3-dihydroxypropyl)-5-[N-(2,3-dihydroxypropyl)acetamido]-2,4,6-triiodoisophthalamide), the crude iohexol is subjected to several crystallization and precipitation procedures in order to remove the lipophilic nonionic impurities (Oslo Symposium, Ion Exchange Solvent Extraction, Paper 49IYAP 1982). Similarly, in Haavaldsen et al. X-Ray Contrast Agents, Acta Pharm. Succ. 20, 219-232 (1983), the preparation of iohexol and other nonionic derivatives of 5-amino-2,4,6-triiodoisophthalamide is described as involving multiple crystallization steps and normal phase preparative liquid chromatography for purification of the desired end products. Such crystallization purification procedures are also described in U.S. Pat. No. 4,250,113, dated Feb. 10, 1981, directed to iohexol and related nonionic compounds and in U.S. Pat. No. 4,001,323, dated Jan. 4, 1977, directed to the nonionic X-ray contrast agent iopamidol (N, N'-bis(1,3-dihydroxypropyl -5-lactylamido-2,4,6-triiodoisophthalamide).

Skjold and Berg (Journal of Chromatography, 366 (1986) 299-309) describe the use of laboratory scale reversed-phase preparative liquid chromatography for the removal of ionic impurities from solutions containing such impurities and water-soluble, nonionic X-ray contrast agents. In the chromatographic process described, the loading ratio of chromatographic packing material to crude product to be purified is on the order of 31.6:1 to 19.6:1 and the mobile phases used for eluting the chromatographic column are mixtures of methanol and water alone or with the addition of ammonium acetate buffers, tetrabutylammonium chloride and phosphate buffer.

Schering AG German patent application P31 10 737 A1, published Oct. 14, 1982, discloses a chromatographic process for the separation and purification of water-soluble, nonionic compounds from solutions containing ionic compounds which employs a silanized separating material, such as silanized silica gel, as the chromatographic packing material and water or water-alcohol mixtures as the eluting solvent. The process is described as being applicable to the separation and purification of water-soluble, nonionic X-ray contrast media from water-soluble inorganic or organic salts.

There remains a need for an efficient and effective factory scale chromatographic process for the decolorization, separation, and purification of water-soluble, nonionic contrast media compounds and MRI agents from solutions containing nonionic compound impurities.

SUMMARY OF THE INVENTION

Among the objects of the present invention may be mentioned the provision of an improved process for the decolorization, reversed phase chromatographic separation, and purification of water-soluble, nonionic contrast media compounds and MRI agents from solutions containing impurities which are nonionic compounds in nature; the provision of such a process which efficiently removes non-polar impurities which are difficult to remove by conventional methods such as crystallization and precipitation; the provision of a process of the type described which can be economically practiced on a factory scale for the production of nonionic contrast media; and the provision of such a process which utilizes lower loading ratios of chromatographic packing material/total wt. nonionic compounds than were heretofore attainable. Other objects and features will be in part apparent and in part pointed out hereinafter.

Briefly, the present invention is directed to a process for the recolorization, reversed phase chromatographic separation, and purification of water-soluble, nonionic contrast media compounds from solutions containing nonionic organic impurities which comprises the steps of:

(a) packing a chromatographic column with a chromatographic packing material;

(b) passing through the column a solution containing a water-soluble, nonionic contrast media compound and nonionic compounds as impurities at a loading ratio between approximately 10 to 1 and 1.5 to 1 wt. packing material/total wt. nonionic compounds; and (c) eluting the column to produce an eluate containing substantially pure, water-soluble, nonionic contrast media compound or MRI agent.

Preferably, the chromatographic packing material is a bonded phase chromatographic packing material such as a silanized material consisting of octadecylsilane bonded to solid silica support particles and having a carbon content between approximately 13 and 16% and a particle size between approximately 37 and 63μ. In addition, a chromatographic packing material in which a stationary phase is not chemically bonded to solid support particles, such as a hydrocarbon impregnated silica gel in which the hydrocarbon is adsorbed onto the surface of the gel, may also be employed.

DESCRIPTION OF THE PREFERRED EMBODIMENTS

In accordance with the present invention, it has now been found that water-soluble, nonionic contrast media compounds and MRI agents may be effectively decolorized, purified, and separated from nonionic compound impurities on a factory scale through a reversed phase chromatographic process in which a chromatographic column is first packed with a chromatographic packing material, preferably a bonded phase chromatographic packing material, such as a silanized packing material consisting of octadecylsilane bonded to solid silica support particles. A chromatographic packing material in which a stationary phase is not chemically bonded to solid support particles may less preferably be used in the practice of the invention. A solution containing a water-soluble, nonionic contrast media compound and nonionic compounds as impurities is then passed through the column at a loading ratio between approximately 10 to 1 and 1.5 to 1 wt. packing material/total wt. nonionic compounds, and the column is eluted to produce a substantially pure, nonionic contrast media compound. The reversed phase chromatographic process of the invention efficiently and economically removes such nonionic, non-polar impurities from the desired nonionic contrast media compounds on a factory scale and at favorable loading ratios not heretofore achievable. The nonionic impurities separated through the process of the invention are generally structurally similar to compounds being purified and cannot be effectively separated therefrom by conventional crystallization, recrystallization and precipitation techniques.

The novel process of the present invention is applicable to the general decolorization and separation of nonionic compound impurities from water-soluble, nonionic contrast media compounds or alternatively, MRI agents. The nonionic contrast media compounds include x-ray contrast media compounds such as N,N'-bis(2,3-dihydroxypropyl)-5-[N-(2-hydroxyethyl)-glycolamido]-2,4,6-triiodoisophthala-mide(ioversol), N,N'-bis(2,3-dihydroxypropyl)-5-[N-(2,3-dihydroxypropyl)acetamidol]-2,4,6-triiodoisophthalamide(iohexol), N,N'-bis(1,3-dihydroxypropyl)-5-lactylamido-2,4,6-triiodoisophthalamide(iopamidol), 2[3-acetamido-2,4,6-triiodo-5-(N-methylacetamido) benzamido]-2-deoxy-D-glucose(metrazamide), N,N'-bis(2,3-hydroxypropyl)-2,4,6-triiodo-5-(2-keto-L-gulonamido)isophthalimide(iogulamide), 5,5'-[malonylbis[(2-hydroxyethyl)imino]]bis[N,N'-bis[2-hydroxy-1-(hydroxymethylethyl]-2, 4,6-triiodoisophthalamide(iodecimol)5,5'-[(2-hydroxytrimethylene)bis(acetylimino)]bis[N,N'-bis(2,3-dihydroxypropyl)-2,4, 6-triiodoisophthalamide(iodixanol), 3-[N-(2-hydroxyethyl) acetamido]-2,4,6-triiodo-5-(methylcarbamoyl)-D-glucoanilide (ioglucol), N,N'-bis(2,3-dihydroxypropyl)-2,4,6-triiodo-5-(N-methylglycolamido)isophthalamide(iomeprol), N,N'-bis(2,3-dihydroxypropyl)-5-[N-(2-hydroxy-3-methoxypropyl)acetamido]-2, 4,6-triiodoisophthalamide(iopentol), N,N'-bis(2,3-dihydroxypropyl)2,4,6-triiodo-5-(2-methoxyacetamido)-N-methylisophthalamide(iopromide), 3,5-diacetamido-2,4,6-triiodo-N-methyl-N[[methyl(D-gluco2,3,4-5,6-pentahydroxyhexyl)carbamoyl]methyl]benzamide(iosarcol), N,N,N',N',N'',N''-hexakis(2-hydroxyethyl)2,4,6-triiodo-1,3,5-benzenetricarboxamide(iosimide), 5,5'[thiobis(ethylenecarbonylimino)]bis[N,N-bis(2,3-dihydroxypropyl) -2,4,6-triiodo-N,N'-dimethylisophthalamide(iotasul), and 5,5'-[malonylbis(methylimino)]bis[N,N'-bis[2,3-dihydroxy-1(hydroxymethyl)propyl]-2,4,6-triiodoisophthalamide(iotrolan).

As used herein, the term "nonionic contrast media compounds" includes, and the present invention is applicable to, nonionic magnetic resonance imaging (MRI) agent ligands and neutral (or nonionic) metal complexes of their ligands with suitable metals from the first, second, or third row transition elements or the lanthanide or actinide series. Typical ligands include N,N''-bis[N-(2,3-dihydroxypropyl) carbamoylmethyl]-diethylenetriamine-N,N',N''-triacetic acid, N, N'-bis[N-(2,3-dihydroxypropyl)carbamoylmethyl]ethylenediamine-N,N'-diacetic acid, N,N'''-bis[N-(2-hydroxyethyl)carbamoylmethyl]triethylenetetraamine-N,N',N'',N'''-tetraacetic acid, N,N''-bis[N-(1-hydroxymethyl-2,3-dihydroxypropyl) carbamoylmethyl]diethylenetriamine-N,N',N''-triaacetic acid and N,N'-bis[N-(2-hydroxyethyl)carbamoylmethyl]ethylenediamine-N, N'-diacetic acid. Examples of various other complexes, nonionic contrast media compounds and MRI agents which may be purified through the process of the invention are known to those skilled in the art.

The chromatographic packing material employed in the practice of the invention is preferably a bonded phase chromatographic material consisting of a stationary phase chemically bonded to solid support particles. The stationary phase may be one of various materials from the group consisting of alkylsilanes, arylsilanes, haloalkylsilanes, alkyl esters, aryl esters, alkyl amines, alkylcyano compounds, alkyldiols, alkyl ethers, aryl ethers, haloalkyl ethers, alkylcarboxylic acids, arylcarboxylic acids, alkysulfonic acids, arylsulfonic acids, polystyrenedivinylbenzene, aminopolycaprolactem, glycidoxyethylmethoxysilzne, and anionic and cationic exchange resins. All of these materials except the anionic and cationic exchange resins are useful to selectively separate nonionic impurities from nonionic contrast media compounds on the basis of oleophilicity. Similarly, the solid support particles may be selected from the group consisting of silica, silica gel, silicic acid, silicon dioxide, alumina, aluminum oxide, glass beads, porous glass, polymers, gels, and polystyrene-divinylbenzene.

Preferably, the chromatographic packing material is a silanized material consisting of an alkylsilane stationery phase, such as octadecylsilane, octylsilane, hexylsilane, butylsilane, methylsilane, trimethylsilane or dimethylsilane, bonded to silica, silica gel, silicic acid or silicon dioxide support particles. The most preferred chromatographic packing material for use in the process of the invention is a silanized material consisting of octadecylsilane bonded to solid silica support particles.

The chromatographic packing material should have an average pore size of 50–300 A, and preferably an average pore size of 100–140 A. Also, it has been found that the chromatographic packing material should have a carbon content of between approximately 5 and 20%, preferably between approximately 13 and 16%. Further, the particle size of the packing material should range between approximately 10 and 500$\mu$, preferably between approximately 20 and 200$\mu$, and more preferably at least 70 wt. % of the packing material should have a particle size between approximately 37 and 63$\mu$. In this latter most preferred range of particle size, it has been found that optimization of loading ratio and separation are achieved.

Exemplary of preferred chromatographic packing materials for use in the present invention are those marketed under the trade designations "YMC ODS-Si" by YMC Company of Morris Plains, N.J. and "Whatman Partisil-40-ODS-3" by Whatman BioSystems, Inc. of Clifton, N.J. "YMC ODS-Si" is a silanized packing material consisting of octadecylsilane bonded to solid silica support particles and has an average pore size of 120±20 A, a carbon content of between approximately 14.5 and 16%, with at least 70% of the material having a particle size between approximately 37 and 63μ. "Whatman Partisil-40-ODS-3" is also a silanized packing material consisting of octadecylsilane bonded to solid silica support particles. Other exemplary chromatography column packing materials which may be used in the practice of the invention include those sold by Waters Chromatography Division of Millipore Corporation of Milford, Mass. and E. Merck Co. of Darnstadt, West Germany and handled by EM Science of Cherry Hills, N.J. among others.

Less preferably, the chromatographic packing material employed in the practice of the invention may be a hydrocarbon impregnated silica gel in which a long chain (e.g. C18) hydrocarbon is not chemically bonded to the silica gel but is adsorbed onto the surface. An exemplary chromatographic packing material of this type is that marketed under the trade designation "RPS, Impregnated 50010 or 50050" by Analtech of Newark, Del. and having a carbon content of about 5%, an average pore size of 60 A and a particle size of 35–75μ. This packing material is compatible with reversed phase eluting solvents such as methanol/water and acetonitrile/water.

The practice of the invention, for purposes of illustration, may be described with respect to the separation and purification of the nonionic X-ray contrast agent ioversol (N,N'-bis(2,3-dihydroxypropyl)-5-[N-(2-hydroxyethyl) glycolamido]-2,4,6-triiodoisophthalamide) from solutions containing nonionic compound impurities such as 5-amino-N,N'-bis (2,3-dihydroxypropyl)-2,4,6-triiodoisophthalamide and N,N'-bis (2,3-dihydroxypropyl)-5-[[N-(2-hydroxyethyl)carbamoyl]-methoxy]-2,4,6-triiodoisophthalamide. In the preparation of ioversol (U.S. Pat. No. 4,396,598, dated Aug. 2, 1983), the crude ioversol product formed from a multistep process is decolorized and deionized by treatment with anionic and cationic exchange resins to remove ionic impurities and produce a crude ioversol product containing the above-named nonionic compound impurities and possibly other nonionic compound impurities.

In order to purify the crude ioversol product, a large chromatographic column is filled with a chromatographic packing material such as a bonded phase chromatographic packing material of the type described above and a water-miscible solvent or a water/water-miscible solvent mixture is passed through the column to wet and condition the packing material. The solvent or solvent mixture may be pumped forwards and backwards through the column in order to remove air and compress the packing material. Any suitable water-miscible solvent such as a lower alkanol (e.g., methanol or isopropanol), acetonitrile, trihydrofuran, methyl ethyl ketone or acetone may be used for this purpose.

The crude ioversol solution containing ioversol and nonionic compound impurities is then passed through the column at a loading ratio between approximately 10 to 1 and 1.5 to 1, preferably 3 to 1, wt. packing material/total wt. nonionic compounds. It is preferred that this step be carried out at a temperature between approximately 0° and 100° C., more preferably between 25° and 40° C., and at a pressure between approximately 5 and 2000 psi, more preferably between 80 and 500 psi, and most preferably between 100 and 200 psi. In general, the lower the temperature employed, the higher the pressure required to pump the crude material being purified through the column, and the higher the temperature employed, the lower the pressure at which the eluting crude solution is pumped or passed through the column. This is due to the fact that the viscosity of the crude material changes along with the temperature change.

The column is then eluted with water or a water/water-miscible solvent mixture to produce an eluate containing substantially pure ioversol or other desired water-soluble nonionic contrast media compound substantially free of the nonionic compound impurities present in the original crude solution, these impurities being retained by the chromatographic packing material. The eluting fluid is preferably water but may also be any water/water-miscible solvent mixture. Here again, any suitable water-miscible solvent may be employed including, for example, lower alkanols (e.g., methanol or isopropanol), acetonitrile, trihydrofuran, methyl ethyl ketone or acetone. Water or a water/methanol mixture are the preferred eluting fluids.

Through the practice of the process of the present invention, it has been found that the purity of the desired nonionic contrast medium compound may be substantially improved from, for example, on the order of about 95% in the crude solution being treated to about 99.7 or 99.8% in the final product. Moreover, the process can be conveniently and economically practiced on a factory scale with large quantities of crude nonionic contrast medium compound being processed at favorable loading ratios without adversely affecting the desired purity level achieved.

Where the chromatographic packing material employed is a material having a silica-containing support, the eluate from the process is desirably passed through ion exchange resin to remove silica therefrom. Also, once the column has been eluted as described, it may then be treated with a water-miscible solvent or a water/water-miscible solvent mixture to remove the nonionic compound impurities therefrom and regenerate the column for reuse. The same water-miscible solvents previously mentioned may be used for this purpose, and the column may be reused a number of times before it becomes exhausted.

The following examples illustrate the practice of the invention.

EXAMPLE 1

A chromatographic column was dry packed until full with a silanized chromatographic packing material consisting of octadecylsilane bonded to solid silica particles (sold under the trade designation "YMC ODS-Si" by YMC Company of Morris Plains, N.J.). Methyl alcohol was then pumped forwards and backwards through the column to remove air and compress the bed. The column was opened three times to refill the voids formed by compression. A total of 148.85 kg. of the silanized chromatographic packing material was used.

The silanized chromatographic packing material was a white to light cream-colored, free-flowing powder having an average pore size of $120+/-20$ A, a carbon content between 13 and 16% and the following particle size distribution:

| | |
|---|---|
| $>63\mu$ | 30 wt. % max. |
| $37-63\mu$ | 70 wt. % min. |
| $<37\mu$ | 2 wt. % max. |

A solution containing crude N,N'-bis(2,3-dihydroxypropyl)-5-[N-(2-hydroxyethyl)glycolamide]-2,4,6-triiodoisophthalamide (ioversol) and as impurities the nonionic compounds 5-amino-N,N'-bis(2,3-dihydroxypropyl)-2,4,6-triiodoisophthalamide (designated hereafter as Sample A) and N,N'-bis(2,3-dihydroxypropyl)-5-[[N-(2-hydroxyethyl)-carbamoyl]-methoxy]-2,4,6-triiodoisophthalamide (designated hereafter as Sample B) was passed through the column at the loading ratios set forth in Table 1 below. The column was then twice eluted with water at the temperatures and water volumes set forth in Table 1. The loading ratios set forth in Table 1 are the ratios of wt. packing material/total wt. nonionic compounds. The eluate or effluent from each of the runs set forth passed the limits with respect to the content of Sample A and Sample B nonionic impurities present.

The eluate from each run from the column was sequentially passed through a small stainless steel column containing one liter of IRA-458 ion exchange resin and then through a polypropylene column containing five liters of IR-120 ion exchange resin in order to remove silica which had been released from the chromatographic column during elution. The eluate was then passed through a depyrogenating ultrafilter attached in series with the column containing the IR-120 resin.

EXAMPLE 2

A large chromatographic column was packed with 170 kg. of a silanized packing material consisting of octadecylsilane bonded to solid silica particles (marketed under the trade designation "ODS 340" by Whatman) and having a particle size between 40 and 80μ. Methyl alcohol (380 l.) was pumped through the column to wet the packing material, and water was pumped through the column for 16 hours at a rate of 12 l/min. to condition the packing material.

A 50% w/v solution (55 l.) of crude ioversol and containing Sample A and Sample B as nonionic compound impurities was pumped into the column at a rate of 3 l/min. This volume of solution contained about 27 kg. of crude Ioversol. The loading ratio was 7:1 wt. packing material/total wt. nonionic compounds. Water (1140 l.) was pumped through the column at a rate of 12 l/min. The first 190 l. of eluate was discarded. The next 570 l. of eluate was collected, and the solution was stripped from the eluate to give 24.3 Kg. of solid, pure ioversol (yield 90%). The next 380 l. of eluate was collected, and the solution was stripped from the eluate to give about 2 kg. of impure ioversol which was again subjected to the chromatographic purification process.

The purity of the initial crude ioversol was 96%, and the purity of the final ioversol obtained from the chromatographic purification was 99.7%.

EXAMPLE 3

A 24 in. internal diameter×40 in. length stainless steel chromatography column was filled with approximately 375 lbs. of dry silanized chromatographic packing material consisting of octadecylsilane bonded to solid silica particles ("ODS-Si"). A uniform column bed was produced as follows. First, about 110 gal. of methyl alcohol was pumped through the column; and then about 55 gal. of methyl alcohol was pumped backward through the column. Next about 110 gal. of methyl alcohol was pumped forward through the column; and then about 25 gal. of methyl alcohol was pumped backward through the column. Finally, about 80 gal. of methyl alcohol was pumped forward through the column. This process forced air from the packing material and compacted it, leaving an empty space at the top of the column. The empty space was filled with more dry ODS-Si packing material, and process water was pumped through the column for at least 2 hours. The process of adding packing material to the empty head space and pumping process water through the column was repeated until the packing material no longer compressed. The column holds a total of 420–440 lbs. of packing material when completely packed.

A solution containing approximately 60 lbs. of ioversol and containing Sample A and Sample B as nonionic impurities was pumped through a 0.2 micron filter onto the chromatographic column. The loading ratio of packing material/total wt. nonionic compounds was approximately 7:1. A mixture of water and methanol was then pumped through the column to elute the product.

The first 125 gal. of effluent or eluate from the chromatographic column was passed through a column containing Amberlite IRA-458 ion exchange resin, another column containing Amberlite IR-120 plus ion exchange resin, and then through an ultrafiltration unit to remove any silica released from the chromatographic column during elution. This first fraction, which contained 80–90% of the purified ioversol, was collected in a receiver tank.

A second fraction of approximately 125 gal. was eluted from the chromatographic column and contained most of the remaining ioversol. This fraction was collected in a second receiver tank.

The chromatographic column was then flushed with a mixture of methyl alcohol and water which contained at least 50% methyl alcohol to remove nonionic compound impurities from the column and regenerate the column for reuse. The column was then reequilibrated with process water before reuse in chromatographing additional portions of solution containing ioversol and Sample A and Sample B as nonionic compound impurities. In eluting the column as before, additional first and second fractions were collected in first and second receiver tanks as previously described.

The combined first chromatography fractions containing purified ioversol were concentrated using a wiped-film evaporator. Two passes through the evaporator were required to obtain the desired 50–75% w/v concentration. As the first fractions from the chromatography column are collected, they are passed through the evaporator and collected in a hold tank. After all the material from a concentrated deionized ioversol solution production batch had been chromatographed as described, the combined concentrated first fraction material was passed through the evaporator a second time. This twice concentrated solution was collected in a closed receiver and tested for Sample A and Sample B content. If the solution has a Sample A content ≦0.1 area % and a Sample B content ≦0.5 area %, the material is then spray dried to obtain the final bulk substance Ioversol.

The combined second fractions from the repeated elutions described above were concentrated using a wiped-film evaporator. As the second fractions from the chromatographic column were collected, they were passed through an evaporator and collected in a hold tank. After all the material from a concentrated, deionized ioversol solution production batch had been chromatographed as described, the combined concentrated second fraction material was passed through the evaporator a second time. This twice concentrated solution was collected in a receiver and tested. If the solution has a Sample A content ≦0.1 area % and a Sample B content ≦0.5 area %, the material is combined with the first chromatography fractions described above for spray drying. If the solution has a Sample A content >2 area % and/or a Sample B content >5 area %, it is discarded. If the solution has a Sample A content between 0.1 and 2 area % and/or a Sample B content between 0.5 and 5 area %, the solution is combined with another solution of crude ioversol solution for chromatographic purification as described above. This process illustrates that the combined second fraction material may be further reprocessed by recycling into the original column feed provided sufficient overall quality is maintained.

EXAMPLE 4

Two chromatographic columns packed with a silanized packing material (~800 g) consisting of octadecylsilane bonded to solid silica particles were attached in series to a Waters preparative chromatograph. The columns were flushed with 3-6 liters of methanol and then flushed with 3-6 liters of water. 500 g. of N,N'-bis-(2,3-dihydroxypropyl)-2,4,6-triiodo-5-(2-keto-L-gulonamido)isophthalamide (iogulamide) containing nonionic compound impurities were dissolved in 5000 ml. of water. The solution was pressure filtered through 3μ and 0.45μ cartridge filters in series. The solution was then passed through the columns at 50-100 ml. min. and the effluent collected. When all of the solution was on the columns, the columns were eluted with deionized water at the rate of 150-200 ml./min.

It was found that the purity of the final, eluted iogulamide compound was >99.0% whereas the purity of the initial MP-10013 compound was 97.8%. The average yield obtained from the chromatographic purification was 91.8%.

After carrying out the chromatographic purification, the columns were flushed with 3 liters of methanol to remove the nonionic impurities and regenerate the columns with depyrogenated and deionized water for re-use.

In view of the above, it will be seen that the several objects of the invention are achieved and other advantageous results attained.

As various changes could be made in the above process without departing from the scope of the invention, it is intended that all matter contained in the above description or shown in the accompanying drawings shall be interpreted as illustrative and not in a limiting sense.

What is claimed is:

1. A process for the reversed phase chromatographic decolorization, separation, and purification of water-soluble, nonionic contrast media compounds from solutions containing nonionic compound impurities, said solutions having been treated for removal of ionic impurities; comprising the steps of:
   (a) packing a chromatographic column with a chromatographic packing material;
   (b) passing through said column a solution containing a water-soluble, nonionic contrast media compound and nonionic compounds as impurities at a loading ratio between approximately 10 to 1 and 1.5 to 1 wt. packing material/total wt. nonionic compounds; and
   (c) eluting said column to produce an eluate containing substantially pure, water-soluble, nonionic contrast media compound.

2. A process as set forth in claim 1 wherein said chromatographic packing material is a bonded phase chromatographic packing material consisting of a stationary phase chemically bonded to solid support particles.

3. A process as set forth in claim 2 wherein said stationary phase is selected from the group consisting of alkylsilanes, arylsilanes, haloalkylsilanes, alkyl esters, aryl esters, alkyl amines, alkylcyano compounds, alkyldiols, alkyl ethers, aryl ethers, haloalkylethers, alkylcarboxylic acids, arylcarboxylic acids, alkylsulfonic acids, arylsulfonic acids, polystyrenedivinylbenzene, aminopolycaprolactem, glycidoxy-ethyl-methoxysilane, and anionic and cationic exchange resins.

4. A process as set forth in claim 3 wherein said alkylsilane is selected from the group consisting of octadecylsilane, octylsilane, hexylsilane, butylsilane, methylsilane, trimethylsilane, and dimethylsilane.

5. A process as set forth in claim 3 wherein said alkylsilane is octadecylsilane.

6. A process as set forth in claim 2 wherein said solid support particles are selected from the group consisting of silica, silica gel, silicic acid, silicon dioxide, alumina, aluminum oxide, glass beads, porous glass, polymers, gels, and polystyrenedivinylbenzene.

7. A process as set forth in claim 6 wherein said solid support particles are silica.

8. A process as set forth in claim 1 wherein said chromatographic packing material is a silanized material consisting of octadecylsilane bonded to solid silica support particles.

9. A process as set forth in claim 1 wherein said chromatographic packing material is one in which a stationary phase is not chemically bonded to solid support particles.

10. A process as set forth in claim 9 wherein said chromatographic packing material is a hydrocarbon impregnated silica gel in which said hydrocarbon is adsorbed onto the surface of said gel.

11. A process as set forth in claim 1 wherein sad chromatographic packing material has an average pore size of approximately 50-300 A.

12. A process as set forth in claim 1 wherein said chromatographic packing material has an average pore size of approximately 100-140 A.

13. A process as set forth in claim 1 wherein said chromatographic packing material has a carbon content of between approximately 5 and 20%.

14. A process as set forth in claim 1 wherein said chromatographic packing material has a carbon content of between approximately 13 and 16%.

15. A process as set forth in claim 1 wherein said chromatographic packing material has a particle size between approximately 10 and 500μ.

16. A process as set forth in claim 1 wherein a major proportion of said chromatographic packing material has a particle size between approximately 20 and 200μ.

17. A process as set forth in claim 1 wherein at least 70 wt. % of said chromatographic packing material has a particle size between approximately 37 and 63μ.

18. A process as set forth in claim 1 wherein said water-soluble, nonionic contrast media compound is an x-ray contrast media compound selected from the group consisting of N,N'-bis(2,3-dihydroxypropyl)-5-[N-(2-hydroxyethyl)glycolamido]-2,4,6-triiodoisophthalamide, N,N'-bis(2,3-dihydroxypropyl)-5-[N-(2,3- dihydroxypropyl)acetamido]-2,4,6-triiodoisophthalamide, N,N'-bis(1,3-dihydroxypropyl)-5-lactylamido-2,4,6-triiodoisophthalamide, 2[3-acetamido-2,4,6-triiodo-5-(N-methylacetamido)benzamido]-2-deoxy-D-glucose, N,N'-bis(2,3-hydroxypropyl)-2,4,6-triiodo-5-(2-keto-L-gulonamido)isophthalimide, 5,5'-[malonylbis[(2-hydroxyethyl)imino]]bis[N, N'-bis[2-hydroxy-1-(hydroxymethyl)ethyl]-2,4,6-triiodoisophthalamide, 5,5'-[(2-hydroxytrimethylene)bis(acetylimino)]bis[N,N'-bis(2,3-dihydroxypropyl)-2,4,6-triiodoisophthalamide, 3-[N-(2-hydroxyethyl)acetamido]-2,4,6-triiodo-5-(methylcarbamoyl)-D-gulcoanilide, N,N'-bis(2,3-dihydroxypropyl)-2, 4,6-triiodo-5-(N-methylglycolamido)isophthalamide, N,N'-bis(2,3-dihydroxypropyl)-5-[N-(2-hydroxy-3-methoxypropyl) acetamido]-2,4,6-triiodoisophthalamide, N,N'-bis(2,3-dihydroxy propyl)-2,4,6-triiodo-5-(2-methoxyacetamido)-N-methylisophthalamide, 3,5-diacetamido-2,4,6-triiodo-N-methylN[-[methyl(D-gluco-2,3,4,5,6-pentahydroxyhexyl)carbamoyl]methyl]benzamide, N,N,N',N',-N'',N''-hexakis(2-hydroxyethyl)-2,4,6-triiodo-1,3,5-benzenetricarboxamide, 5,5'[thiobis(ethylenecarbonylimino)]-bis[N,N-bis(2,3-dihydroxypropyl)-2,4,6-triiodo-N, N'-dimethylisophthalamide, and 5,5'-[malonyl-bis(methylimino)]bis[N,N'-bis[2,3-dihydroxy-1(hydroxymethyl)propyl]-2,4,6-triiodoisophthalamide.

19. A process as set forth in claim 1 wherein said water-soluble, nonionic contrast media compound is the x-ray contrast media compound N,N'-bis(2,3-dihydroxypropyl)-5-[N-(2-hydroxyethyl)glycolamido]-2,4,6-triiodoisophthalamide and said nonionic compound impurities are 5-amino-N,N'-bis(2,3-dihydroxypropyl)-2,4,6-triiodoisophthalamide and N,N'-bis(2, 3-dihydroxypropyl)-5-[[N-(2-hydroxyethyl)-carbamoyl]methoxy]-2,4,6-triiodoisophthalamide.

20. A process as set forth in claim 1 wherein said water-soluble, nonionic contrast media compound is a magnetic resonance imaging agent ligand or ligand complex.

21. A process as set forth in claim 1 wherein said water-soluble, nonionic contrast media compound is a magnetic resonance imaging agent ligand selected from the group consisting of N,N'''-bis[N-(2,3-dihydroxypropyl) carbamoylmethyl]diethylenetriamine-N,N',N''-triacetic acid, N,N'-bis[N-(2,3-dihydroxypropyl)carbamoylmethyl]ethylenediamine N,N'-diacetic acid, N,N'''-bis[N-(2-hydroxyethyl)carbamoylmethyl]triethylenetetraamine-N,N',N'',N'''-tetraacetic acid, N,N''-bis[N-(1-hydroxymethy-2,3-dihydroxypropyl) carbamoylmethyl]diethylenetriamine-N,N',N''-triacetic acid and N,N'-bis[N-(2-hydroxyethyl)carbamoylmethyl]ethylenediamine-N,N'diacetic acid.

22. A process as set forth in claim 1 wherein said loading ratio is approximately 3 to 1 wt. packing material/total wt. nonionic compounds.

23. A process as set forth in claim 1 wherein said column is eluted with a material selected from the group consisting of water and a water/water-miscible solvent mixture.

24. A process as set forth in claim 1 wherein said column is eluted with a water/lower alkanol mixture.

25. A process as set forth in claim 24 wherein said column is eluted with a water/methanol mixture.

26. A process as set forth in claim 1 wherein said column is eluted with water.

27. A process as set forth in claim 1 wherein steps (b) and (c) are carried out at a temperature between approximately 0° and 100° C.

28. A process as set forth in claim 1 wherein steps (b) and (c) are carried out at a temperature between approximately 25° and 40° C.

29. A process as set forth in claim 1 wherein the eluate produced in step (c) is passed through ion exchange resin to remove silica therefrom.

30. A process as set forth in claim 1 wherein prior to step (b) a material selected from the group consisting of a water-miscible solvent and a water/water-miscible solvent mixture is passed through said chromatographic column to condition said chromatographic packing material.

31. A process as set forth in claim 30 wherein said water-miscible solvent is methanol.

32. A process as set forth in claim 1 wherein subsequent to step (c) said column is treated with a material selected from the group consisting of a water-miscible solvent and a water/water-miscible solvent mixture to remove said nonionic compound impurities therefrom and regenerate said column for reuse.

33. A process as set forth in claim 32 wherein said water-miscible solvent is methanol.

34. A process for the separation and purification of the nonionic X-ray contrast media compound N,N'-bis(2,3-dihydroxypropyl)-5-[N-(2-hydroxyethyl)-glycolamido]-2,4,6-triiodoisophthalamide from solutions containing nonionic compound impurities including 5-amino-N,N'-bis(2,3-dihydroxypropyl)-2,4,6-triiodoisophthalamide and N,N'-bis (2,3-dihydroxypropyl)-5-[[N(2-hydroxyethyl)-carbamoyl]methoxy] -2,4,6-triiodoisophthalamide comprising the steps of:

(a) packing a chromatographic column with a silianized chromatographic packing material consisting of octadecylsilane bonded to solid silica support particles;

(b) passing through said column a solution containing said nonionic X-ray contrast media compound and said nonionic compound impurities at a loading ratio of approximately 3 to 1 wt. packing material/total wt. nonionic compounds; and (c) eluting said column with water to produce an eluate containing substantially pure N,N'-bis(2,3-dihydroxypropyl)-5-[N-(2-hydroxyethyl)-glycolamido]-2,4,6-triiodoisophthalamide.

* * * * *